US008776621B2

(12) United States Patent
Modic et al.

(10) Patent No.: US 8,776,621 B2
(45) Date of Patent: Jul. 15, 2014

(54) FLUID SAMPLE DELIVERY SYSTEM AND METHOD

(75) Inventors: Walter D. Modic, Sunnyvale, CA (US); Michael McAdams, Los Gatos, CA (US); Lawrence T. McNary, San Jose, CA (US); Trung K. Huynh, Milpitas, CA (US); Christopher A. Pohl, Union City, CA (US); Frank Hoefler, Mountain View, CA (US)

(73) Assignee: Dionex Corporation, Sunnyvale, CA (US)

( * ) Notice: Subject to any disclaimer, the term of this patent is extended or adjusted under 35 U.S.C. 154(b) by 677 days.

(21) Appl. No.: 12/399,786

(22) Filed: Mar. 6, 2009

(65) Prior Publication Data

US 2010/0224012 A1 Sep. 9, 2010

(51) Int. Cl.
*G01N 1/22* (2006.01)
(52) U.S. Cl.
USPC ....................................... 73/863.23
(58) Field of Classification Search
USPC ....................................... 73/864.01
See application file for complete search history.

(56) References Cited

U.S. PATENT DOCUMENTS

| 3,693,804 A | 9/1972 | Grover |
| 3,902,372 A | 9/1975 | MacKinnon |
| 3,918,913 A | 11/1975 | Stevenson et al. |
| 4,164,765 A * | 8/1979 | Gysling ........................ 360/92.1 |
| 4,287,155 A | 9/1981 | Tersteeg et al. |
| 4,470,315 A | 9/1984 | Ellgehausen et al. |
| 4,527,438 A | 7/1985 | Fosslien |
| 4,586,546 A | 5/1986 | Mezei et al. |
| 4,644,807 A | 2/1987 | Mar |
| 4,774,058 A | 9/1988 | Mehl |
| 4,813,287 A | 3/1989 | Walzel et al. |
| 4,854,355 A | 8/1989 | Chazot et al. |

(Continued)

FOREIGN PATENT DOCUMENTS

| DE | 198 54 565 A1 | 5/2000 |
| EP | 0 955 078 A1 | 11/1999 |

(Continued)

OTHER PUBLICATIONS

"Porex® Chromatography Media", 2007, two pages, Porex Corporation, Fairburn, GA (accessed at http://www.porex.com/pdf/Chromatography%20Media.pdf).

(Continued)

*Primary Examiner* — Peter Macchiarolo
*Assistant Examiner* — Alex Devito
(74) *Attorney, Agent, or Firm* — Victor Johnson

(57) ABSTRACT

A fluid delivery system including a filter for filtering solid particles from a liquid sample, the filter including a first filter member configured to filter solid media from a liquid sample, a second filter member fluidly connected to the first filter member, and a third filter member fluidly connected to a downstream end of the second filter member. The second filter member is configured to filter relatively smaller solid media from the liquid sample than the first filter member, and the third filter member is configured to filter relatively larger solid media from the liquid sample than the second filter member. In various aspects, the system includes a displacement-type plunger needle to draw sample fluid from a vial, a cantilevered carousel for rotatably supporting an array of sample holding vials, and a support for supporting the carousel. Method of using the fluid delivery system are also disclosed.

15 Claims, 9 Drawing Sheets

(56) References Cited

U.S. PATENT DOCUMENTS

| | | | |
|---|---|---|---|
| 4,895,808 A | 1/1990 | Romer | |
| 5,314,825 A | 5/1994 | Weyrauch et al. | |
| 5,368,729 A | 11/1994 | Stefkovich et al. | |
| 5,567,309 A | 10/1996 | Classon et al. | |
| 5,595,653 A | 1/1997 | Good et al. | |
| 5,595,707 A | 1/1997 | Copeland et al. | |
| 5,622,869 A | 4/1997 | Lewis et al. | |
| 5,700,427 A | 12/1997 | Ghaed et al. | |
| 5,980,616 A | 11/1999 | Johnson et al. | |
| 6,119,533 A | 9/2000 | Gherson et al. | |
| 6,171,280 B1 | 1/2001 | Imazu et al. | |
| 6,197,001 B1 * | 3/2001 | Wilson et al. | 604/157 |
| 6,270,726 B1 | 8/2001 | Tyberg et al. | |
| 6,492,183 B1 | 12/2002 | Perman et al. | |
| 6,500,671 B2 | 12/2002 | Hage et al. | |
| 7,300,801 B2 | 11/2007 | Pranis et al. | |
| 7,482,169 B2 | 1/2009 | Gjerde et al. | |
| 7,700,042 B2 | 4/2010 | Matsumoto et al. | |
| 2002/0045861 A1 * | 4/2002 | Tribe | 604/154 |
| 2002/0146840 A1 | 10/2002 | Hage et al. | |
| 2003/0064008 A1 | 4/2003 | Hage et al. | |
| 2003/0226792 A1 | 12/2003 | Tumbrink et al. | |
| 2004/0069076 A1 | 4/2004 | Gamble | |
| 2004/0072375 A1 | 4/2004 | Gjerde | |
| 2004/0265173 A1 | 12/2004 | Matsumoto et al. | |
| 2006/0090576 A1 | 5/2006 | Sander | |
| 2006/0093525 A1 | 5/2006 | Brunner et al. | |

FOREIGN PATENT DOCUMENTS

| | | |
|---|---|---|
| EP | 1 933 154 A2 | 6/2008 |
| FR | 2 063 695 | 7/1971 |
| GB | 2 392 854 A | 3/2004 |
| JP | 2004-333259 A | 11/2004 |
| JP | 2006-515562 A | 6/2006 |
| WO | WO 89/00977 A1 | 2/1989 |
| WO | WO 02/053256 A1 | 7/2002 |

OTHER PUBLICATIONS

"Porex® Healthcare Applications", 2006, one page, Porex Corporation, Fairburn, GA (accessed at http://www.porex.com/pdf/InlineFilter_AppCS.pdf).

"Zitex® Filters", date unknown, one page, Saint-Gobain Performance Plastics, Poestenkill, NY.

* cited by examiner

FIG. 2A   FIG. 2B

FLUID SAMPLE DELIVERY SYSTEM AND METHOD

BACKGROUND OF THE INVENTION

1. Field of the Invention

This invention relates, in general, to a fluid delivery system for delivering samples to a chromatographic column and methods for their use.

2. Description of Related Art

A number of different techniques have heretofore been employed for delivering liquid samples to chromatographic columns. Such techniques employ a hollow needle which draws fluid into a syringe through a filter. The sample is thereafter delivered to the column.

Existing systems for delivering liquid samples typically use a single filter composed of a microporous material or membrane. An exemplar of a conventional filter is U.S. Pat. No. 5,567,309 to Classon et al. which shows a filter having a filter cap with a thin membrane covering an opening on the bottom of the cap. The thin membrane is formed of a microporous element housed in a filter receptacle and has a porosity between 0.1 and 1 microns. The filter may include a multiple layer construction formed of multiple, different, thin membrane layers. The filter membrane(s) are thin to allow for a higher flow rate through the filter. As such, the Classon system sacrifices filtering capacity. Moreover, because Classon makes use of a thin filter, the filter is likely to become clogged and obstructed more often which leads to increased downtime.

There is also a need to provide a system which more efficiently accesses liquid sample from a plurality of sample holding vials. Conventional techniques lack automation and require a user to identify a vial and control the system to access the identified vial.

In light of the foregoing, it would be beneficial to have methods and apparatuses which overcome the above and other disadvantages. It would be desirable to provide a system with higher-efficiency filtering performance. It would be desirable to provide a system with less downtime for filter cleaning and replacement.

It would be desirable to provide a system with greater efficiency for accessing and delivery fluid samples.

BRIEF SUMMARY OF THE INVENTION

In summary, various aspects of the present invention are directed to a filtering device for a fluid sample delivery apparatus, the filter including a first filter member configured to filter solid media from a liquid sample, a second filter member, an upstream end of the second filter member fluidly connected to a downstream end of the first filter member, and a third filter member, an upstream end of the third filter member fluidly connected to a downstream end of the second filter member. The second filter member is configured to filter relatively smaller solid media from the liquid sample than the first filter member and the third filter member is configured to filter relatively larger solid media from the liquid sample than the second filter member.

In various embodiments, the first filter member and/or the third filter member are longer than the second filter member in the direction of flow. The first filter member and/or the third filter member may be configured to filter media having a particle size between about 30 microns and about 200 microns. The second filter member may be configured to filter media having a particle size between about 0.1 microns and about 2 microns.

In various embodiments, the one or more filter members are formed of fluoropolymers or porogens. In various embodiments, at least the first filter member and second filter member are formed into a unitary structure.

Various aspects of the present invention are directed to a sample holding container including a sample holding vial for holding liquid sample, and a plunger slideably mounted in the sample holding vial. The plunger includes a filter through which the sample is delivered as the sample is drawn.

Various aspects of the present invention are directed to a method of filtering a liquid sample, the method including providing a filtering device, introducing a liquid sample into an upstream end of the filtering device, and flowing the liquid sample through the filtering device such that the liquid sample flows sequentially through the first filter member, the second filter member, and the third filter member sequentially. The solid media is filtered from the liquid sample during the flowing through the filtering device.

Various aspects of the present invention are directed to a sample delivery apparatus including a fluid sample delivery apparatus for drawing a fluid sample from a sample holding vial, the sample delivery device including a plunger needle configured to displace sample fluid from the vial into the sample delivery apparatus, a cantilevered carousel for rotatably supporting an array of sample holding vials along a circumference of the carousel and positioning at least one of the sample holding vials below the fluid sample delivery apparatus, and a support for supporting the carousel immediately adjacent the fluid sample delivery apparatus when the delivery apparatus is inserted into the respective vial.

In various embodiments, the support is positioned below the carousel. The support may be a load-bearing roller bearing positioned below the carousel. The plunger needles may apply a load to the carousel in a direction substantially orthogonal to the carousel surface and the support may be positioned below the carousel in a substantially opposite direction.

Various aspects of the present invention are directed to a sample delivery apparatus including a plurality of sample holding vials, a fluid sample delivery apparatus including a plunger for insertion into one of the plurality of sample holding vials and drawing a fluid sample from the respective vial, the amount of fluid sample drawn corresponding to the depth of insertion of the plunger in the respective vial, sample delivery measuring means for measuring the amount of sample drawn based on the plunger insertion in the respective vial, and storing means for storing information related to the amount of sample drawn from the respective vial.

In various embodiments, the method in accordance with the present invention includes providing a fluid sample delivery apparatus, storing information related to the volume of the plurality of sample holding vials, drawing fluid from one of the plurality of sample holding vials, and updating the volume information for the respective holding vial from which sample is drawn.

In various embodiments, the method further includes determining an amount of sample required, and selecting a sample holding vial from the plurality of sample holding vials based on the required sample amount and the stored information.

The fluid sample delivery apparatus may further include a motor for driving the plunger into the respective vial, a motor monitor for monitoring information related to at least one of a load on the motor during driving, a speed of the plunger during driving, or both, and an error detector for detecting an obstruction in a sample delivery flowpath based on the monitored information.

Various aspects of the present invention are directed to a method of continuously filtering a liquid sample using a fluid delivery apparatus, the method including providing a fluid sample in a sample holding vial, drawing the fluid sample from the sample holding vial with a fluid delivery apparatus, filtering the fluid sample through the filtering device, and collecting the filtered fluid sample. The fluid delivery apparatus optionally includes a plunger needle configured to reciprocate within the sample holding vial thereby driving fluid sample into a fluid passageway of the fluid delivery apparatus, a motor for applying a driving force to the plunger needle, and a filtering device positioned the fluid passageway, the filtering device being configured to filter solid waste from the fluid sample. The fluid delivery apparatus may be configured to adjust the motor driving force in response to a predetermined condition.

In various embodiments, the motor is a stepper motor and the predetermined condition is based on motor slippage. In various embodiments, the predetermined condition is based on needle speed.

In various embodiments, the filtering device includes a first filter member configured to filter solid media from a liquid sample, a second filter member, an upstream end of the second filter member fluidly connected to a downstream end of the first filter member, and a third filter member, an upstream end of the third filter member fluidly connected to a downstream end of the second filter member. The second filter member is configured to filter relatively smaller solid media from the liquid sample than the first filter member and the third filter member is configured to filter relatively larger solid media from the liquid sample than the second filter member.

The fluid delivery system and method of the present invention have other features and advantages which will be apparent from or are set forth in more detail in the accompanying drawings, which are incorporated in and form a part of this specification, and the following Detailed Description of the Invention, which together serve to explain the principles of the present invention(s).

BRIEF DESCRIPTION OF THE DRAWINGS

FIG. 2A is a centerline sectional view of the sample delivery needle and sample holding vial of FIG. 1B, illustrating the needle above the sample holding vial. FIG. 2B is a centerline sectional view of the sample delivery needle and sample holding vial of FIG. 1B, illustrating the needle in the sample holding vial and drawing fluid.

DETAILED DESCRIPTION OF THE INVENTION

Reference will now be made in detail to the various embodiments of the invention(s), examples of which are illustrated in the accompanying drawings. While the invention(s) will be described in conjunction with the various embodiments, it will be understood that they are not intended to limit the invention(s) to those embodiments. On the contrary, the invention(s) are intended to cover alternatives, modifications and equivalents, which may be included within the spirit and scope of the invention(s) as defined by the appended claims.

Figure 1A:
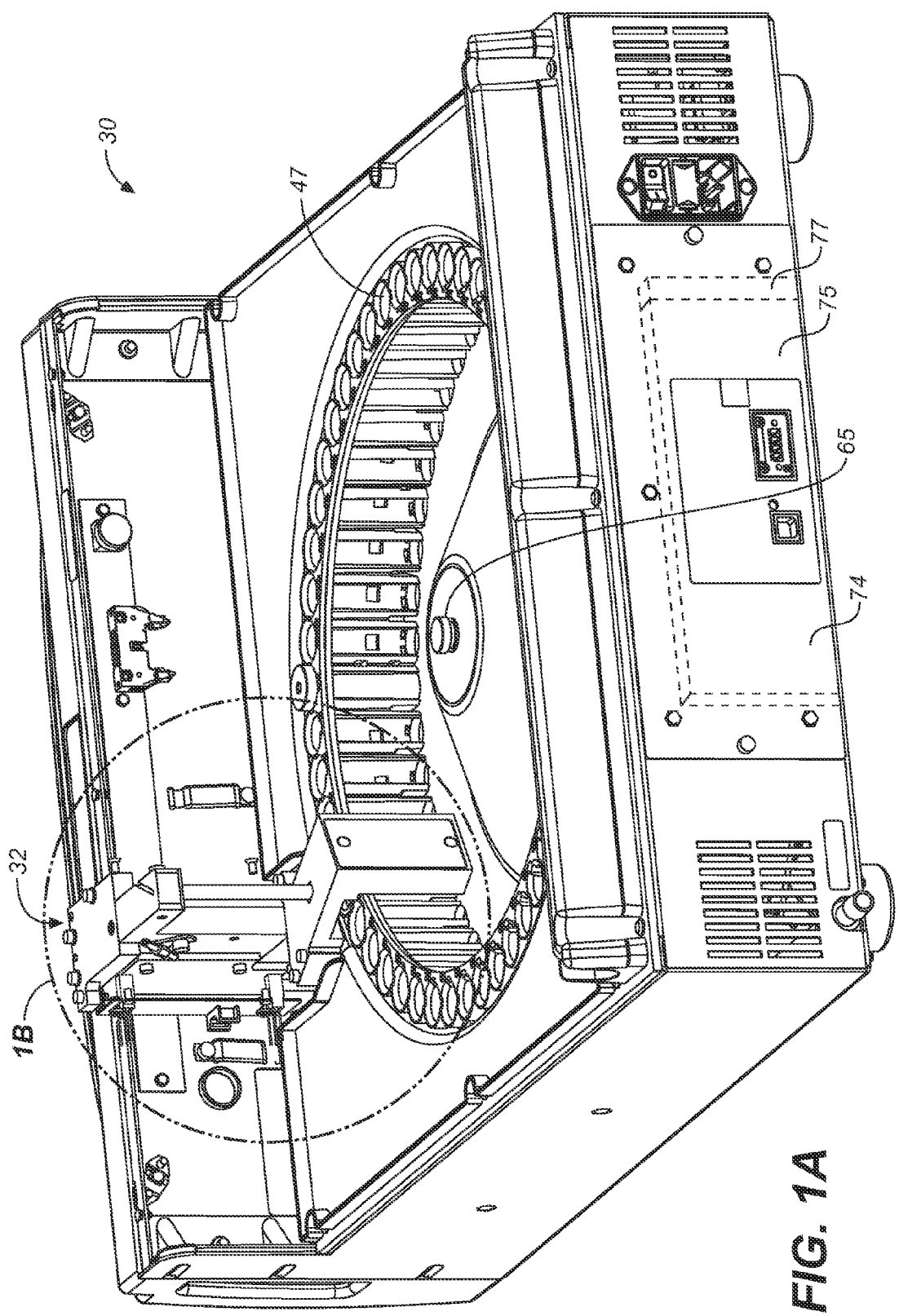
FIG. 1A is a perspective view of a fluid sample delivery system in accordance with the present invention, illustrating an inside of the system with the top lid removed.
Figure 1B:
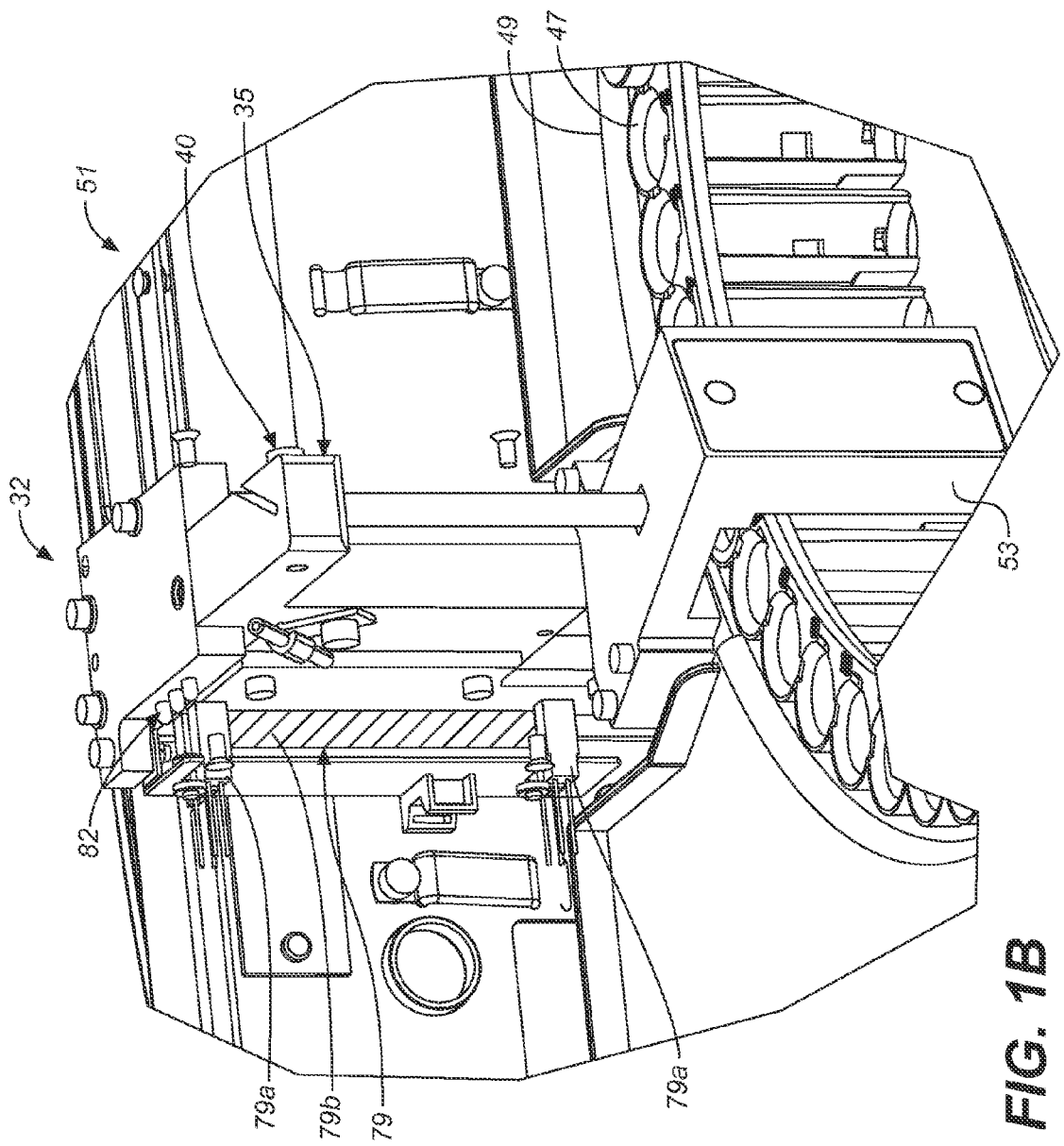
FIG. 1B is an enlarged detail view of the sample delivery assembly and sampling station of the system of FIG. 1, illustrating a needle engaged with a sample holding vial on a carousel.

Turning now to the drawings, wherein like components are designated by like reference numerals throughout the various figures, attention is directed to FIGS. 1-2 which illustrate a sample fluid delivery system, generally designated 30. In various respects, system 30 is similar to the AS40 Autosampler manufactured and sold by Dionex Corporation of Sunnyvale, Calif.

System 30 includes a fluid delivery assembly, generally designated 32. The fluid delivery assembly includes a needle 33 operated by a needle actuator assembly 35 and a fluid passageway. The actuator assembly includes a motor 37, robotic arm 39, and drivetrain or drive assembly 40. The system is configured such that fluid is drawn from a respective vial 44 through a filter device 42 into the needle assembly from where it is delivered to a chromatography column or other component. The needle assembly may include a conventional needle and syringe. Although system 30 has been described with reference primarily to a liquid chromatography system, one will appreciate that the system may be configured for other applications.

The system includes a plurality of sample holding vials 44 configured to hold a liquid sample 46. In various embodiments, each vial 44 is configured to mate with a vial socket of a vial slot 47 on a sample carousel 49. The carousel aligns a respective vial with a sampling station 51 which corresponds to the fluid sample delivery assembly location. Fluid delivery assembly 32 includes a carousel guide device 53 having a track for guiding the vials on the carousel below the needle. In various embodiments, the guide device is configured to lock a vial in place during operation of needle 33.

Sampling station 51 optionally includes a heater for heating the sample. The system may further include other stations such as a rinsing station for rinsing the fluid sample delivery assembly and/or rinsing empty sample holding vials and a mixing station.

The exemplary system is a negative displacement removal system, meaning, fluid is actively displaced from the sample holding vials. One will appreciate, however, that the system in accordance with various aspects of the present invention may be configured to draw fluid using a pump and other conventional means.

Sample holding vial 44 and needle 33 are similar in various respects to U.S. Pat. No. 4,644,807 to Mar (the '807 patent), the entire content of which is incorporated herein for all purposes by this reference. The needle is configured to seal to the sample holding vial when drawing fluid. "Needle" and "plunger needle" will be used interchangeably herein.

With reference to FIGS. 2-4, a plurality of filter caps 54 are provided to enclose each of sample holding vials 44. The cap encloses the vial and protects the sample from exposure to the environment. Various aspects of the cap are similar to those with conventional negative-displacement-type sample removal systems such as the ones disclosed by the '807 patent. The cap is configured to act as a plunger when depressed by the needle. The cap includes a fluidic tube configured to mate to the top of the cap for directing the sample from the filter to the needle. The exemplary cap includes a small aperture above the filter to be engaged by the needle.

In various embodiments, needle 33 is slidably mounted in vial 44 in fluid sealing engagement with side walls of the vial. The plunger has an axially extending passageway through which fluid is delivered when the plunger is depressed or moved toward the bottom of the vial. The fluid sample is pressurized within the vial as the plunger is depressed or moved toward the bottom of the vial. As the plunger displaces fluid in the vial, the fluid sample is urged into the needle. Vial 44 and needle 33 can be fabricated by extrusion, molding, or another suitable process.

The vial and plunger are particularly suitable for use in an automated system in which a plurality of samples are to be delivered to a chromatographic column. The vials can be mounted in vial slots 47 on carousel 49. Each vial slot is moved to sampling station 51 by rotation of the carousel to a location where fluid delivery assembly 32 is located.

As sample is drawn from needle 33 into vial 44, the liquid sample flows through a filter to remove undesirable solid particles. In the illustrated embodiment, the filter is a microporous polymer. The filter removes particulate matter from the sample delivered from sample holding vial 44 through the passageway and is substantially impervious to vapors when needle 33 is at rest.

Figure 2C:
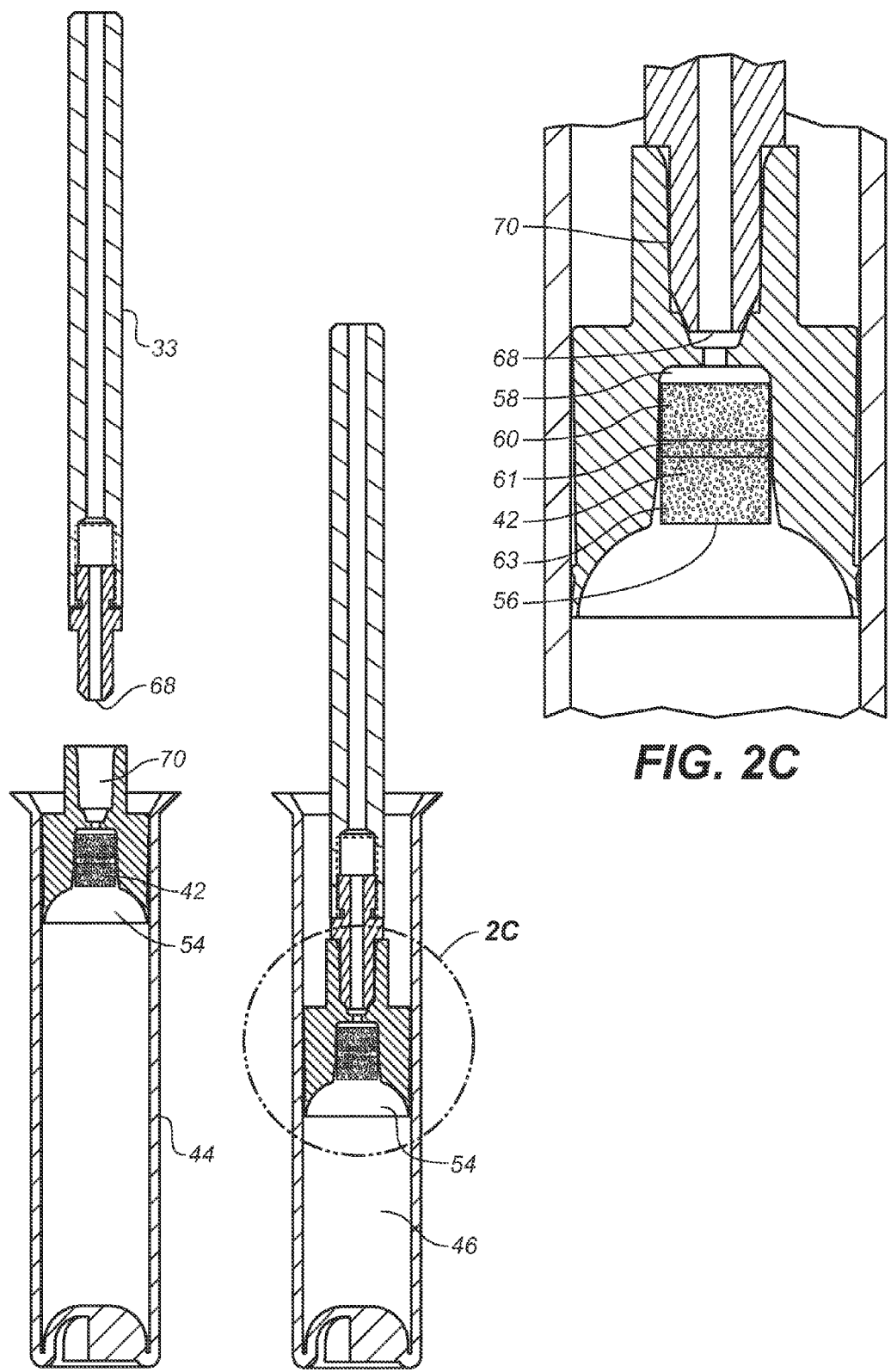
FIG. 2C is an enlarged detail view of the needle of FIG. 2B, illustrating the needle engaging the filter in accordance with the present invention.

In various embodiments and with references to FIGS. 2A-2C, filter 42 is mounted in a counterbore at the lower end of filter cap 54. Filter 42 may installed in the filter cap with mechanical fasteners, interference fit, chemical bonding, and the like.

When installed, the filter has an entrance 56 and exit 58 and a passageway therebetween. In various embodiments, the filter may be installed in either direction, meaning, fluid may flow in either direction.

The filter pore size is to be understood as generally used in the art. The average pore size of the filter may be on the order of about three to about five times the size of the target solid particle to be retained. For example, a 0.45 µm filter may be provided to filter out 0.45 µm particles, but the actual pore size may be larger thereby allowing some 0.45 µm particles to flow through the filter. Thus, the filtering capacity of the filter is to be understood in terms of the particle size intended to be retained and efficiency of the filter in retaining such a particle size.

Figure 3A:
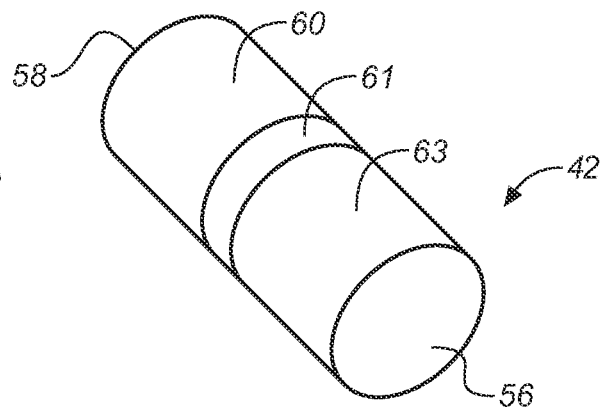
FIG. 3A is a perspective view of the filter of FIGS. 1 and 2.
Figure 3B:
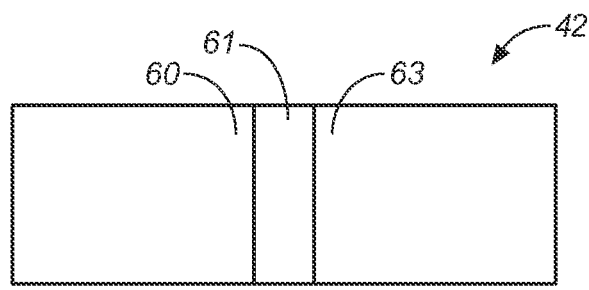
FIG. 3B is a side view in a longitudinal direction of the filter of FIG. 3A.
Figure 3C:
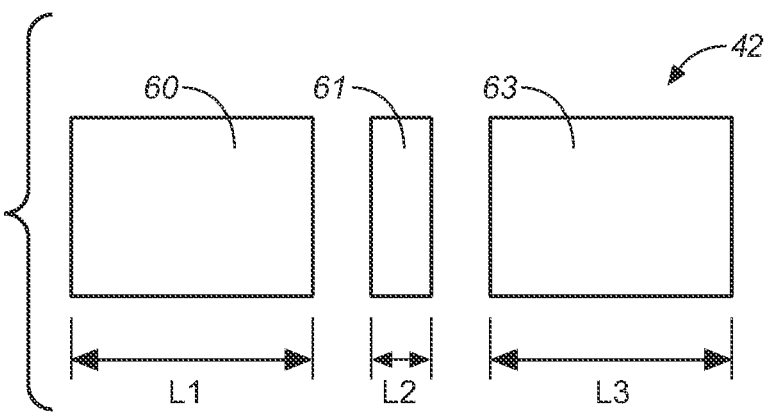
FIG. 3C is an exploded view of the filter of FIG. 3A.
Figure 4A:
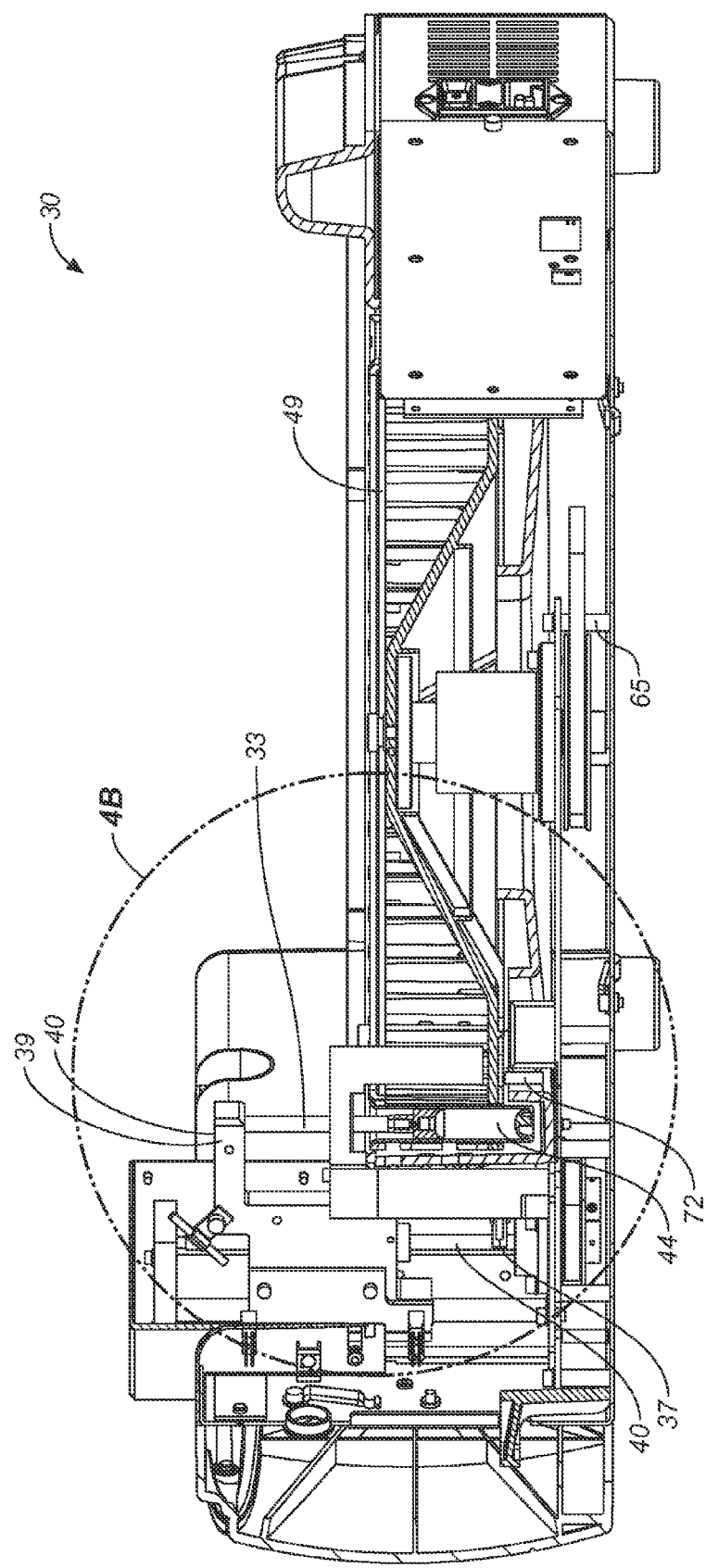
FIG. 4A is a centerline sectional view of the fluid sample delivery system of FIG. 1, illustrating the carousel supported by a carousel support during operation.
Figure 4B:
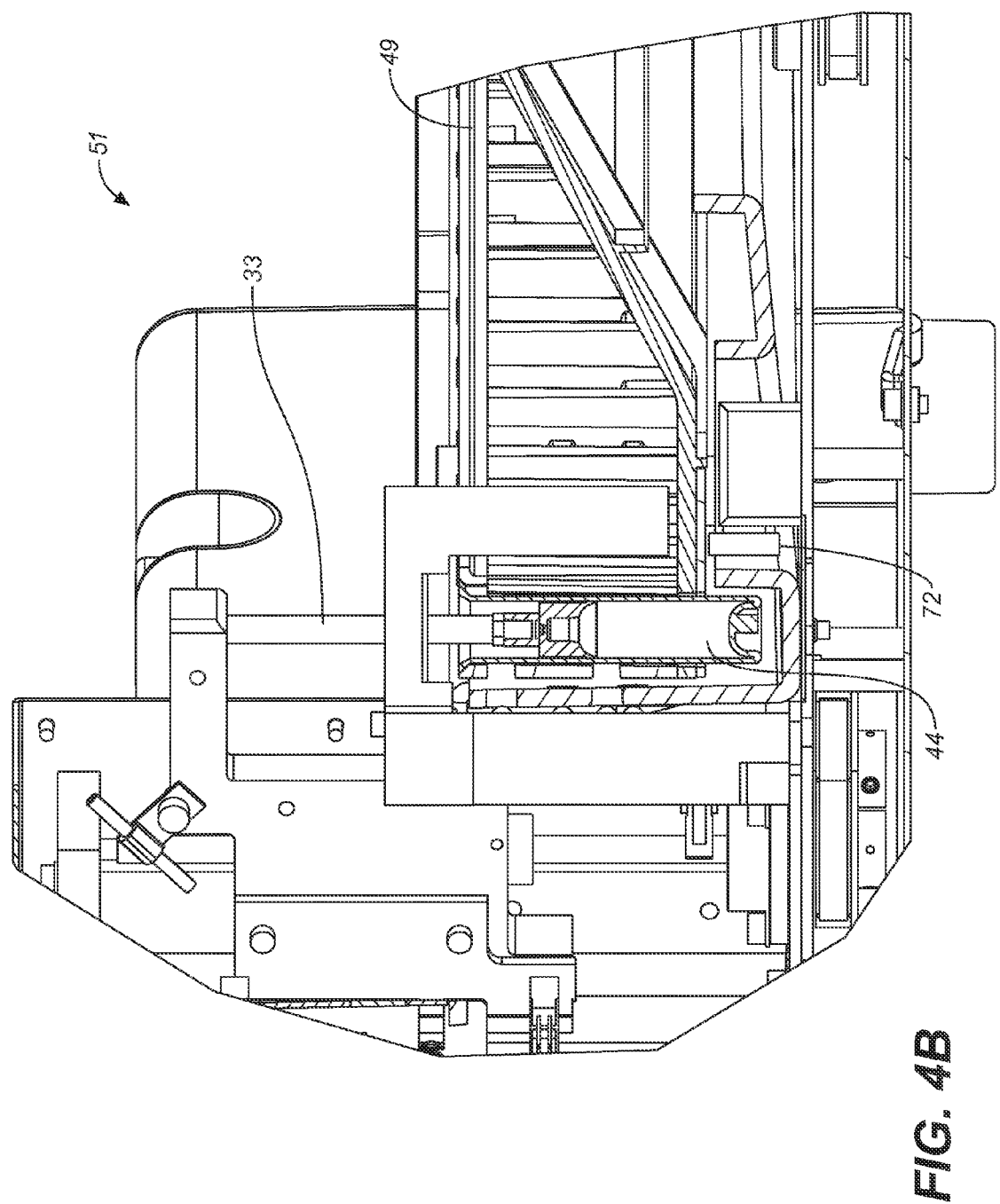
FIG. 4B is an enlarged detail view of the fluid delivery assembly and a portion of the sample holding vial carousel of FIG. 4A.

As shown in FIGS. 3A-3C, filter 42 includes multiple extraction media. In various embodiments, the extraction media are bonded together with adhesives or thermo-welded. In various embodiments, the extraction media are molded together. In various embodiments, the extraction media are compressed together by support members, such as filter screens, within a housing structure.

Exemplary filter 42 includes a first filter member 60, second filter member 61, and third filter member 63, each configured to filter solid media from a liquid sample. An upstream end of the second filter member is fluidly connected to a downstream end of the first filter member. Likewise, an upstream end of the third filter member is fluidly connected to a downstream end of the second filter member.

Second filter member 61 is configured to filter relatively smaller solid media from the liquid sample than first filter member 60. Third filter member 63 is configured to filter relatively larger solid media from the liquid sample than the second filter member. Dimensionally, the second filter member is shorter than the first and third filter members in the direction of flow or axial direction. The first member has a length of L1. The second member has a length of L2. The third member has a length of L3. In the exemplary filter, the filter members thus have a long-short-long configuration. In the exemplary embodiment, L2 is 0.1 mm, L1 is 3.18 mm, and L3 is 3.18 mm.

In various embodiments, the first and third filter members have substantially the same porosity and the second filter member has a smaller porosity. In various embodiments, first filter member 60 and/or third filter member 63 are configured to filter media having a particle size between about 30 microns and about 200 microns. In various embodiments, second filter member 61 is configured to filter media having a particle size between about 0.1 microns and about 2 microns. In various embodiments, the porosity of the first filter membrane is about ten times larger than the porosity of the second filter member. In various embodiments, the first filter membrane is configured to remove solid particles about ten times larger than the second filter member.

Although the exemplary filter is described in terms of an upstream end and downstream end, one will appreciate that the exemplary filter may not be directional and may be placed in the cap in either direction. "Upstream" and "downstream" are used for convenience to describe a direction of the fluid flow after the filter has been mounted in the system.

In various embodiments, first filter member 60 is configured as a pre-filter for second filter member 61 to remove larger particles before they reach the second filter member. With this configuration, the smaller second filter has to extract fewer large particles. Whereas, the first filter member is efficient at extracting large particles, the second filter member is more efficient at filtering smaller particles. In this manner, fluid flows quicker through filter 42 because the first and second filter members are generally only required to filter out particles in their effective range.

With exemplary filter 42, at least first filter member 60 and second filter member 61 are formed into a unitary structure by thermo-welding or other suitable methods. In various embodiments, the first, second, and third filter members are formed into a unitary structure. In various embodiments, the first, second, and third filter members are monolithically formed.

Suitable materials for the filter include, but are not limited to, polytetrafluoroethylene (PTFE), polyethylene (PE), polypropylene (PP), polycarbonate (PCTE), and polyester (PETE), nylon, and other chemically and/or biologically compatible materials. In various embodiments, the filter is formed from fluoropolymers. In various embodiments, the filter is formed from silica within an inert matrix of polytetrafluoroethylene (PTFE). In various embodiments, the filter is formed from a thermo-responsive polymer (TRPs). In various embodiments, the filter is pre-treated to enhance the filtering process. In various embodiments, the filter is pre-treated with alcohol. One will appreciate that the first, second, and third filter members may be formed of the same or different materials. In an exemplary embodiment, first filter member 60 and third filter member 63 comprise polyethylene and second filter member 61 comprises polypropylene. One will appreciate that the filter material may depend in part on the application such as the sample subject.

With reference to FIGS. 1A-1C and 4A-4B, carousel 49 for selectively delivering vials 44 to sampling station 51 will now be described. In operation and use, the carousel includes a an array of sample holding vials along a circumference and rotates to deliver a selected sample holding vial to sampling station 51. In various embodiments, the carousel is disc-shaped and mounted to the system for rotation about its central axis. The plurality of sample holding vials are positioned in respective vial slots along a circumference of the carousel. Each vial slot is configured to receive and secure a sample holding vial.

Carousel 49 is rotatably mounted on a central axis. The carousel is connected to a drive motor 65 through a bearing and drivetrain. The drive motor controls rotation of the carousel.

A portion of the circumference of the carousel is guided through sampling station 51. In the sampling station, arm 39 engages needle 33 and drives the needle towards the vial in the station.

In operation and use, liquid sample 46 is held in vial 44 and cap 54 is configured to close the vial. The cap includes a skirt 67 configured to provide a seal between the cap and the side wall of the vial. Filter 42 generally prevents evaporation of the sample through the cap and passageway.

Sample 46 is discharged from vial 44 by a downward stroke of needle 33 and cap 54. The cap does not begin to move until a tip 68 of the needle is fully seated in a socket 70 of the cap (best shown in FIG. 2B). When the plunger begins to move, any air trapped in the vial above the sample is discharged first. Once the delivery of the sample begins, it continues until the required sample amount has been drawn or the vial is empty.

Exemplary vial 44 and cap 54 are configured such that when the needle is retracted the cap remains in the lowest displacement position in the vial. Thus, the needle presses the cap into the vial but is withdrawn from the vial without the cap. The cap remains in the vial with the sample pressurized below the cap. In one embodiment, the vial includes a bottom portion configured to fit tightly with cap 54. When the needle sampling tip is retracted, the cap is held in the bottom portion of the vial due to the tight fit and the needle separates from the cap. In various embodiments, the vial and cap are configured to reduce "dead space" in the vial. The bottom of the exemplary vial has a shape corresponding to the cap such that substantially all of the fluid is displaced from the vial when the cap contacts the bottom.

As described above, liquid sample 46 is urged into the needle passageway as the needle displaces fluid in the vial with a downward force. The cap is depressed in the vial by means of needle tip 68 which is engageable with an upper portion of the cap and movable between axially extended and retracted positions. The needle tip has a plug which mates with socket 70 to form a fluid-tight seal. The needle tip has an axially extending passageway which communicates with a passageway of the system.

Because sample 46 is drawn by providing a downward axial force to cap 54 and vial 44 with a plunger-like action, carousel 49 is subjected to high axial loading in the region of sampling station 51. As described above, a central axis of the carousel is rotatably mounted to a hub such that the carousel is cantilevered.

To counteract the load forces on the carousel, the exemplary carousel includes a support 72 for supporting the carousel adjacent fluid sample delivery assembly 32 when the needle is driven into the vial. The support is optionally positioned below the carousel. Plunger needle 33 applies a load to the carousel in a direction substantially orthogonal to the carousel surface, and the support is positioned below the carousel facing in a substantially opposite direction.

In the exemplary embodiment, support 72 is a load-bearing roller bearing. The support may also be another rolling support as would be understood by one of skill in the art from the foregoing. Absent the support, the carousel hub would be subjected to a high moment which can lead to binding of the hub axle. The support also minimizes tilting of the cantilevered hub. Because the system measures the amount of sample drawn by the depth of needle displacement, the support minimizes errors caused by movement of the carousel and vial in response to pressure from the needle.

With reference to FIGS. 1A-1C and 4A, system 30 includes a control system 74, which includes a computer processor 75, I/O board (not shown), and computer storage device 77. The computer process controls operation of the system.

In various embodiments, control system 74 is connected to carousel 49 and sampling station 51. The carousel drive motor is operated by a controller in response to commands from control system 74. In the exemplary embodiment, the control system receives data signals from a sensor device connected to the needle assembly and needle motor.

In various embodiments, system 30 includes a metering stage to control the amount of sample drawn from each vial. Since the amount of liquid sample discharged is directly proportional to downward movement of needle 33 and arm 39, the amount of sample drawn can be precisely determined with each downward stroke. The exemplary system includes a measuring device for recording the amount of sample drawn based on the displacement of the needle. The measuring device is incorporated into the control system and receives a signal from motor 37 driving the needle.

Storage device 77 stores information about each of the sample holding vials loaded into the system. The system optionally has bar code readers positioned to read bar codes on the sample holding vials or vial vial slot. The bar codes and reader may be provided as verification means. They may also be used for automated loading of vials. For example, the bar codes on the vial may provide information about a sample in a sample holding vial to the system such that a user does not need to enter such information when loading the system.

Figure 5:
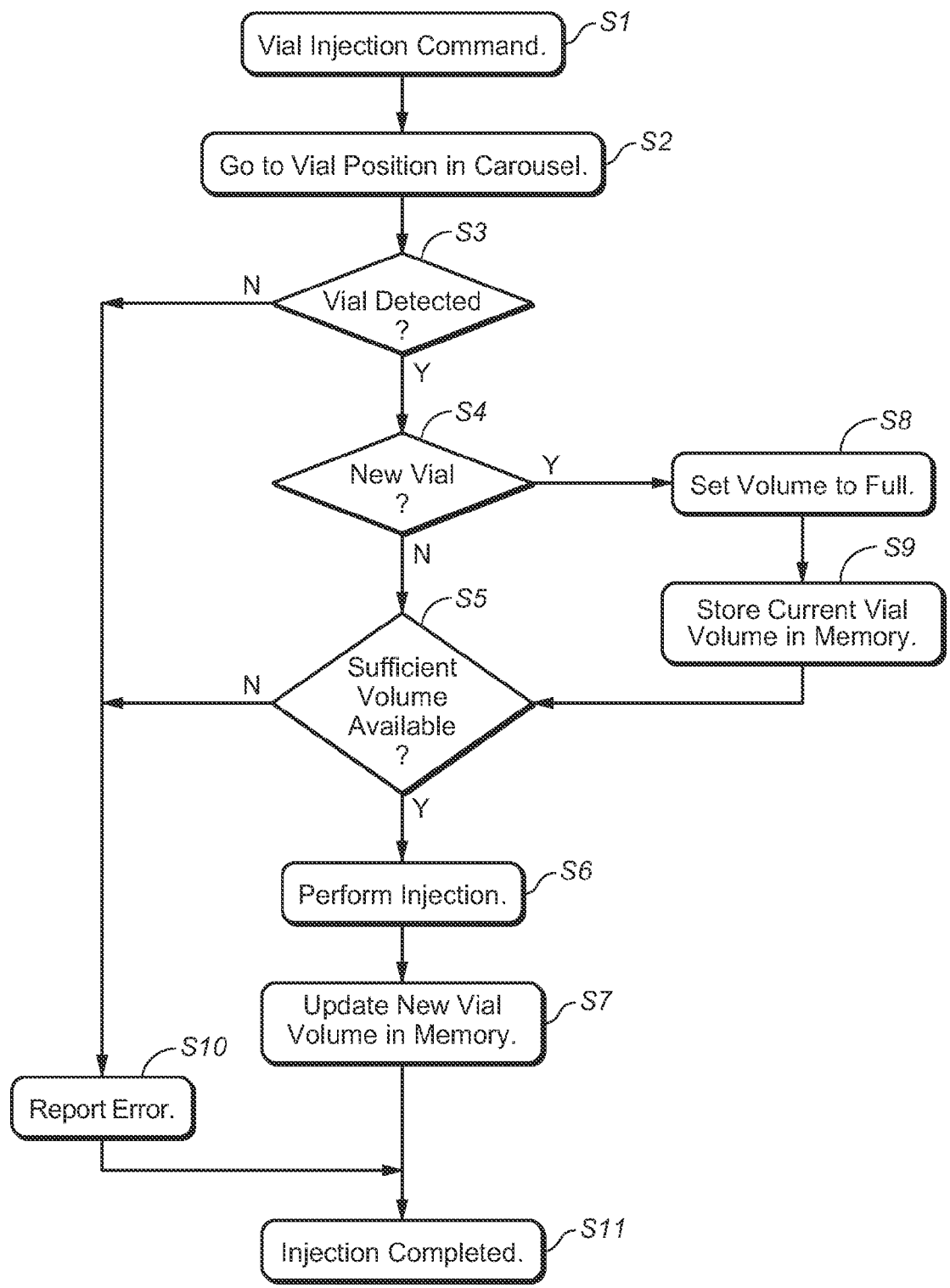
FIG. 5 is a flowchart illustrating operation of the system of FIG. 1, illustrating access and delivery of a sample from a sample holding vial.

Turning to FIG. 5, the method of using the fluid delivery system in accordance with the present invention(s) can now be described. In operation and use, a plurality of sample holding vials 44 are loaded into system 30. Each vial is loaded into a respective vial slot 47 on carousel 49. A selected vial is delivered to sampling station 51 by rotation of the carousel.

As noted above, the amount of sample drawn from a vial can be accurately determined by the displacement depth of the needle in the vial. As such, sample delivery measuring means are provided for measuring the amount of sample drawn. The measuring means can include control system 74 receiving a signal from the needle motor or other suitable measuring means including directly measuring the needle displacement.

Control system 74 and storage device 77 of system 30 store information related to the amount of sample drawn from the respective vial. System 30 includes a database with records for each of the plurality of vials 44 including such information as sample fluid, amount of sample, sample extraction history, and a time stamp. Thus, for each sample drawing event, the system notes the vial which has been accessed and the amount of sample drawn. After each event, the system updates the volume information for the respective holding vial from which sample is drawn. In this manner, the system tracks the amount and type of sample available at any given time. When a user or automated program requires a particular sample, the system can determine from which vial(s) to obtain sufficient sample of that type.

With additional reference to FIG. 5, when a sample is required, control system 74 generates a vial injection command in step S1. Based on the information stored in storage device 77, the system locates an appropriate sample holding vial.

In step S2, control system 74 sends a signal to motor 37 to cause the carousel to rotate until the selected vial slot is in the sampling station. When the selected vial slot is aligned in sampling station 51, a vial detected signal is generated in step S3. If the selected vial slot is empty, an error signal is generated in step S10. The error signal is transmitted to the control system and the storage system updates the vial record.

Turning to step S4, system 30 determines if a new vial is present. With the exemplary system, control system 74 assumes that all vials loaded into the system and detected for the first time are full vials. Accordingly, the system updates the vial record with a volume amount corresponding to a full vial in step S8. In step S9, the new vial information is stored in storage device 77.

In step S5, the control system determines if sufficient sample is available. If the vial is new, the system determines if more sample is needle than available in a full vial. If the vial is an existing vial, the system retrieves sample amount information for the vial from storage device 77. The system then determines if the amount of sample requested exceeds the amount in the vial. If sufficient sample is available, the system proceeds to step S6. If not, the system generates an error signal in step S10.

Once the system has identified and retrieved a vial with sufficient sample as described above, the system performs an injection in step S6. The control system sends an injection command to needle motor 37. The needle motor drives robotic arm 39 and reciprocates needle 33 towards the vial.

Fluid is drawn from the vial by displacement action as described above, and the system records the amount of fluid drawn based on the displacement distance of needle tip 68 in the vial. In step S7, the system records the new volume of the vial based on the initial volume and the amount of sample drawn.

After drawing the fluid, the control system generates an injection complete command in step 11. The system is then ready to receive a new injection command.

In one configuration, the system is pre-loaded with vials and gathers information about each of the vials before operation begins. In this case, the system does not need to search for a vial when operation begins.

Figure 1C:
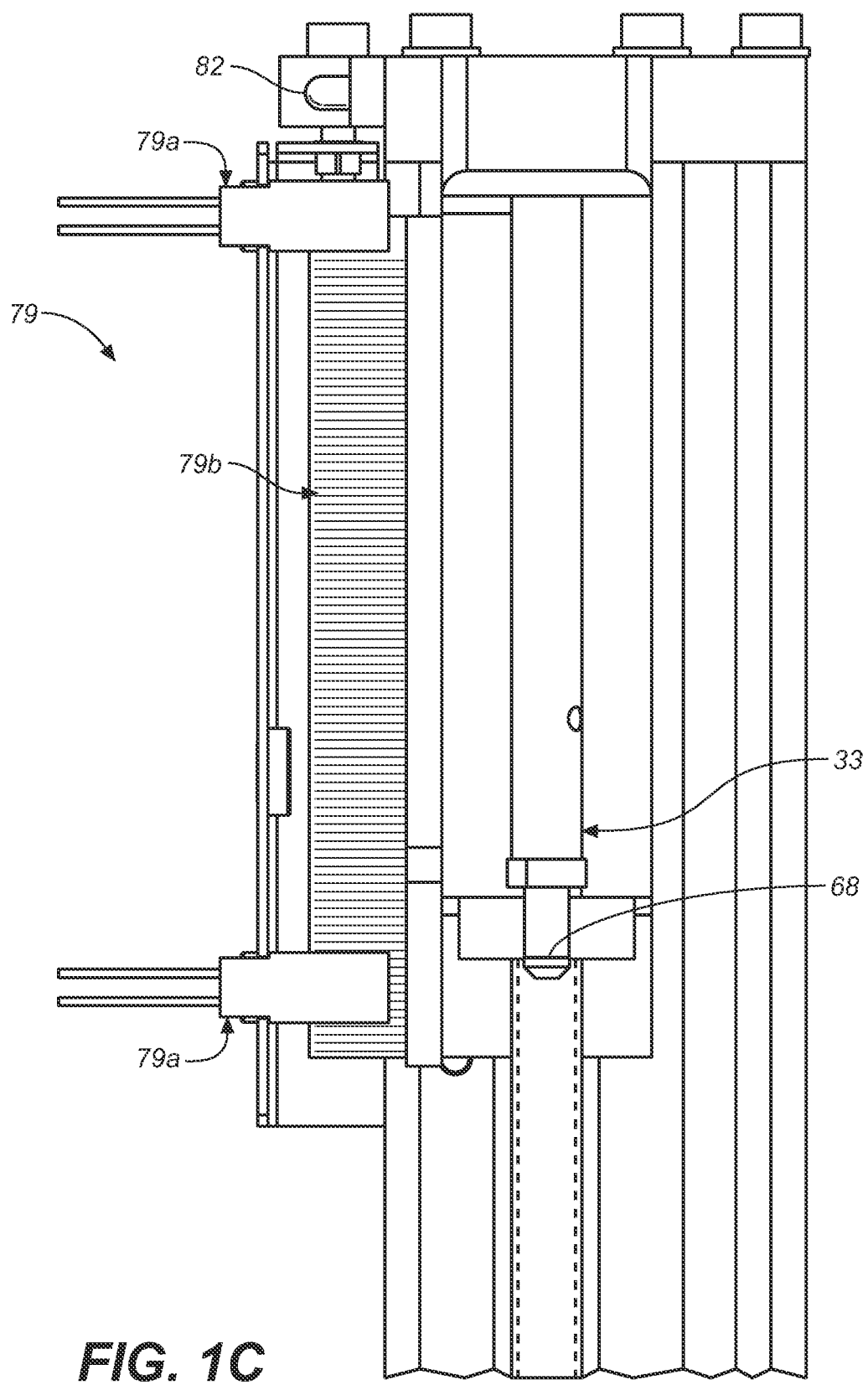
FIG. 1C is an enlarged schematic view of a portion of the sample delivery assembly and sampling station of the system of FIG. 1, illustrating a sensor device for monitoring movement of the needle and controlling fluid delivery in accordance with the present invention.
Figure 6:
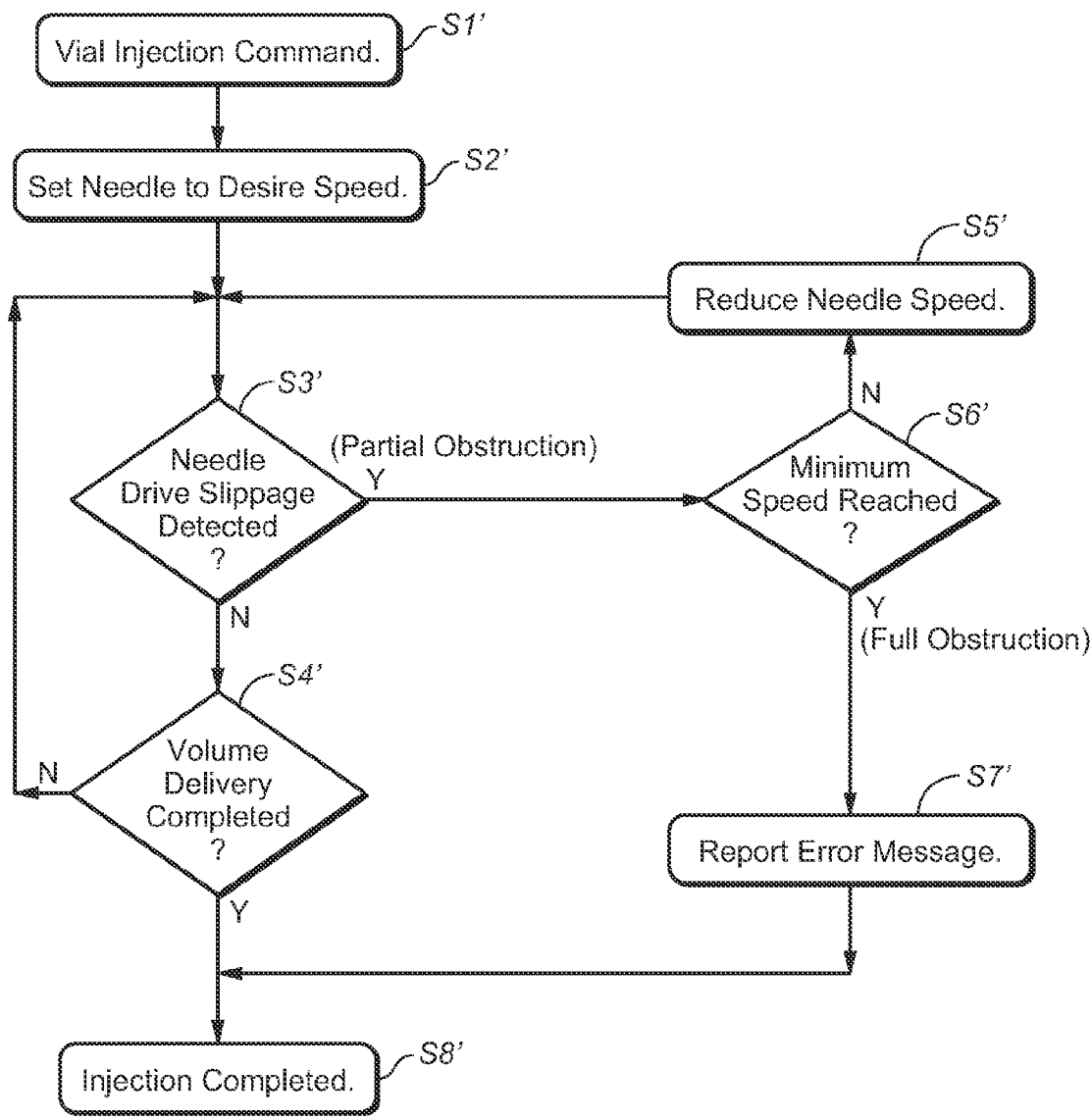
FIG. 6 is a flowchart illustrating operation of the apparatus of FIG. 1, illustrating adjustment of motor speed during the fluid sample delivery process.

Turning now to FIGS. 1C and 6, the operation of sampling station 51, and in particular needle 33, will now be described. In various embodiments, motor 37 driving needle 33 is a stepper motor. A stepper motor driver and a relay operate the stepper motor. In order to draw sample from a vial, the needle reciprocates in an axial direction towards cap 54. The needle tip and cap displace a specified amount of sample from the vial.

As noted above, system 30 can track how much and what type of sample is stored in each sample holding vial 44. Thus, the system can estimate how motor 37 should perform when driving needle 33 into the vial. Based on these principles, the exemplary system detects an obstruction in filter 42 based on deviations from this estimated motor performance.

In various embodiments, stepper motor 37 is attached to a monitor system or sensor for monitoring information related to load (slippage) of the motor during driving, a speed of the plunger needle during driving into the vial, or both. Exemplary system 30 includes at least one optical sensor device 79 connected to stepper motor 37 and control system 74. The sensor device is configured to monitor the motor during operation. The sensor device includes a relay for controlling the motor in response to the motor driver. The optical sensor device also includes a pair of optical sensors 79a for monitoring the motor and generating an error signal when a predetermined threshold or condition is met. For example, the optical sensor device may generate an error signal when motor loading exceeds a specified value corresponding to a partial obstruction in the filter that creates additional backpressure.

In the exemplary embodiment, optical sensor 79 includes an encoder strip 79b configured to be monitored by sensors 79a. In the exemplary system, the encoder strip is a strip of visual markings to be optically detected by the sensors. One will appreciate, however, that other monitoring techniques may be employed in accordance with the invention. As the needle moves, the sensors read the encoder strip to track movement of the needle assembly. Thus, the sensors can determine the position of the needle and the speed of the needle movement. Based on the control signal sent to the motor and the data from the sensors, the control system can determine slippage of the motor.

Referring to FIG. 6, in step S1', control system 74 sends a signal to the stepper motor driver to reciprocate the needle toward a respective vial 44. Needle tip 68 contacts the cap of the vial and drives the cap downward. In step S2', the control system and stepper motor driver set a desired needle speed for displacing the sample.

In step S3', the optical sensor detects whether motor 37 is slipping. In the illustrated embodiment, the motor is a stepper motor and the optical device measures loading on the motor based on slippage. The slippage corresponds to loading on the motor, which in turn corresponds to backpressure from the filter and sample displacement process.

During normal operation, meaning when the passageway has negligible obstruction, the optical sensor sends a signal to the control system indicating that motor slippage is within an acceptable range. The exemplary system includes an optical strip 81 with indicator lights 82 or other suitable means. In various embodiments, one light corresponds to normal operation, and a second light is lit when an error signal is generated based on an obstruction of the passageway as will be described below.

In step S4', the needle is driven into the vial until the specified amount of sample has been withdrawn. Thereafter, an injection complete signal is generated.

When the motor slippage exceeds a threshold value in step S3', the optical sensor sends a passageway obstruction signal to the control system. If the motor slippage is above the normal range but below a predetermined full obstruction value, the control system will determine whether the needle speed is above a minimum speed in step S6'. If the speed is below the minimum speed, a full obstruction of the passageway is determined. Thus, when the motor slippage exceeds a predetermined threshold and the needle speed has dropped below a minimum speed, the system identifies a full obstruction of the passageway. In this case, the system generates an error message in step S7'. By contrast, if motor slippage exceeds a predetermined threshold and the needle speed remains above the minimum speed, the system identifies a partial obstruction of the passageway. In the case of a partial obstruction, the system reduces the needle speed in step S5'. If the system does not periodically detect any movement of the needle in response to motor driving signals, the exemplary system determines a jam has occurred.

In various embodiments, stepper motor 37 has a low-torque mode and high-torque mode. The motor switches from a low-torque mode to the high-torque mode in response to a signal from the controller based on a detected partial obstruction in the filter.

One will appreciate that the threshold motor slippage and needle speed may be adjusted depending on the application and specification requirements. For example, in some cases, it may be desirable to let the system run longer because changing the filter requires downtime. In other cases, it may be desirable to change the filter sooner. Although partial and full obstruction are detected based on a combination of motor slippage and needle speed, one will appreciate that obstructions may be detected and monitored in various other ways as will be understood from the foregoing.

The system has several advantages over existing systems. The system in accordance with the present invention is able to detect obstructions and differentiate between full and partial obstructions. Whereas conventional systems require changing the filter at set intervals, the system allows for substantially continuous operation. Because the exemplary system can detect when full obstructions occur, the system can adjust and continue operating until full obstruction. The signal light also serves as a visual indicator to a user when such full obstruction occurs.

Moreover, system 30 is able to adjust to partial obstructions. As described above, the motor speed may be decreased to reduce backpressure on the motor caused by obstructions. The system will continue operating until a full obstruction is determined.

By adjusting the motor speed, wear and tear on the motor, fluid delivery assembly 32, and other components is also decreased thus extending the life of the parts.

For convenience in explanation and accurate definition in the appended claims, the terms "up" or "upper", "down" or "lower", "inside" and "outside" are used to describe features of the present invention with reference to the positions of such features as displayed in the figures.

The foregoing descriptions of specific embodiments of the present invention(s) have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention(s) and its practical application, to thereby enable others skilled in the art to best utilize the invention(s) and various embodiments with various modifications as are suited to the particular use contemplated. It is intended that the scope of the invention(s) be defined by the Claims appended hereto and their equivalents.

What is claimed is:

1. A sample delivery apparatus comprising:
   a fluid sample delivery device for drawing a fluid sample from a sample holding vial, the fluid sample delivery device including a plunger needle configured to displace sample fluid from the sample holding vial into the sample delivery device by pressurizing the sample fluid within the sample holding vial;
   a cantilevered carousel mounted on a rotating hub, the cantilevered carousel supporting an array of sample holding vials along a circumference of the cantilevered carousel radially outward of the hub and positioning at least one of the sample holding vials at a sampling station below the fluid sample delivery device; and
   a support disposed under the sampling station that only supports a portion of a periphery of the cantilevered carousel within the sampling station immediately adjacent the fluid sample delivery device when the plunger needle is inserted into the respective sample holding vial, wherein a remainder of the periphery of the cantilevered carousel is unsupported.

2. An apparatus according to claim 1, wherein the support is positioned below the carousel.

3. An apparatus according to claim 1, wherein the support is a load-bearing roller bearing positioned below the carousel.

4. An apparatus according to claim 1, wherein the plunger needles applies a load to the carousel in a direction substantially orthogonal to a carousel surface and the support is positioned below the carousel in a substantially opposite direction.

5. The sample delivery apparatus according to claim 1, further comprising:
   a motor for driving the plunger needle into the respective sample holding vial;
   a motor monitor for monitoring information related to at least one of a load on the motor during driving, a speed of the plunger needle during driving, or both; and
   an error detector for detecting an obstruction in a sample delivery flowpath based on the monitored information.

6. The sample delivery apparatus according to claim 1, further comprising:
   sample delivery measuring means for measuring an amount of the liquid sample drawn based on insertion of the plunger needle in the respective sample holding vial; and
   storing means for storing information related to the amount of the liquid sample drawn from the respective sample holding vial.

7. The sample delivery apparatus according to claim 1, wherein the sample holding vial comprises a filter cap having a counterbore at a lower end of the filter cap, and a filter mounted in the counterbore at the lower end of the filter cap.

8. The sample delivery apparatus according to claim 7, wherein the filter comprises:
   a first filter member configured to filter solid media from the liquid sample;
   a second filter member, an upstream end of the second filter member fluidly connected to a downstream end of the first filter member; and
   a third filter member, an upstream end of the third filter member fluidly connected to a downstream end of the second filter member,
   wherein the second filter member is configured to filter relatively smaller solid media from the liquid sample than the first filter member and the third filter member is configured to filter relatively larger solid media from the liquid sample than the second filter member.

9. The sample delivery apparatus according to claim 8, wherein the first filter member and/or the third filter member are longer than the second filter member in the direction of flow.

10. A filtering device according to claim 8, wherein the first filter member and/or the third filter member is configured to filter media having a particle size between about 30 microns and about 200 microns.

11. The sample delivery apparatus according to claim 8, wherein the second filter member is configured to filter media having a particle size between about 0.1 microns and about 2 microns.

12. The sample delivery apparatus according to claim 8, wherein the one or more filter members are formed of fluoropolymers or porogens.

13. The sample delivery apparatus according to claim 8, wherein at least the first filter member and second filter member are formed into a unitary structure.

14. A method of filtering a liquid sample using the sample delivery apparatus according to claim 7, the method comprising:
   providing a fluid sample in the sample holding vial;
   drawing the fluid sample from the sample holding vial with the fluid delivery device;
   filtering the fluid sample through the filter; and
   collecting the filtered fluid sample,
   wherein the fluid delivery device is configured to adjust a driving force in response to a predetermined condition.

15. A method of filtering a liquid sample using the sample delivery apparatus according to claim 8, the method comprising:
   providing a fluid sample in the sample holding vial;
   drawing the fluid sample from the sample holding vial with the fluid delivery device;
   filtering the fluid sample through the filter such that the liquid sample flows sequentially through the first filter member, the second filter member, and the third filter member; and
   collecting the filtered fluid sample,
   wherein the fluid delivery device is configured to adjust a driving force in response to a predetermined condition.

* * * * *